US011103025B2

(12) United States Patent
Liu et al.

(10) Patent No.: US 11,103,025 B2
(45) Date of Patent: Aug. 31, 2021

(54) HEADBAND AND MULTIFUNCTIONAL HELMET

(71) Applicant: DONGGUAN LUCKY SONICS CO., LTD., Guangdong (CN)

(72) Inventors: Jingang Liu, Guangdong (CN); Ming Fang, Guangdong (CN); Zhigang Zhou, Guangdong (CN)

(73) Assignee: DONGGUAN LUCKY SONICS CO., LTD., Guangdong (CN)

( * ) Notice: Subject to any disclaimer, the term of this patent is extended or adjusted under 35 U.S.C. 154(b) by 134 days.

(21) Appl. No.: 16/293,590

(22) Filed: Mar. 5, 2019

(65) Prior Publication Data

US 2019/0191813 A1 Jun. 27, 2019

Related U.S. Application Data

(63) Continuation-in-part of application No. PCT/CN2018/101884, filed on Aug. 23, 2018.

(30) Foreign Application Priority Data

Oct. 27, 2017 (CN) .......................... 201711021804.X

(51) Int. Cl.
*A42B 3/30* (2006.01)
*A42B 3/04* (2006.01)
(Continued)

(52) U.S. Cl.
CPC ............... *A42B 3/306* (2013.01); *A42B 3/04* (2013.01); *A42B 3/044* (2013.01); *A42B 3/0433* (2013.01);
(Continued)

(58) Field of Classification Search
CPC .. A42B 3/306; A42B 3/30; A42B 3/04; A42B 3/044; A42B 3/0433; A42B 3/085;
(Continued)

(56) References Cited

U.S. PATENT DOCUMENTS

2005/0201585 A1* 9/2005 Jannard .................. G02C 11/10
381/381
2007/0106172 A1* 5/2007 Abreu .................. A61B 5/0002
600/549
(Continued)

FOREIGN PATENT DOCUMENTS

CN 1033723 A 7/1989
CN 105996273 A 10/2016
(Continued)

OTHER PUBLICATIONS

International Search Report for Corresponding International Application No. PCT/CN2018/101884 (5 Pages).

*Primary Examiner* — Gary Jackson
*Assistant Examiner* — Sebastian X Lukjan
(74) *Attorney, Agent, or Firm* — Lucas & Mercanti, LLP

(57) ABSTRACT

The present disclosure relates to the field of riding equipment, and particularly to a headband and a multifunctional helmet. The headband comprises a strap configured to bind a head, an adjustment assembly that adjusts the tightness of the strap, and an electronic device that endows the headband with intelligent properties. The strap is connected to the adjustment assembly, and the electronic device is disposed within the adjustment assembly and connected to the adjustment assembly. The headband is an accessory of the helmet, electronic devices are combined with the headband such that the headband has electronic functions associated therewith, expanding the use range of the headband.

16 Claims, 6 Drawing Sheets

(51) Int. Cl.
*A42B 3/08* (2006.01)
*A61B 5/00* (2006.01)
*H04B 1/3827* (2015.01)
*A61B 5/0205* (2006.01)
*A61B 5/024* (2006.01)
*A61B 5/369* (2021.01)

(52) U.S. Cl.
CPC ................ *A42B 3/085* (2013.01); *A42B 3/30* (2013.01); *A61B 5/0205* (2013.01); *A61B 5/6803* (2013.01); *H04B 1/385* (2013.01); *A61B 5/02438* (2013.01); *A61B 5/369* (2021.01)

(58) Field of Classification Search
CPC ........ A42B 3/145; A42B 3/066; H04B 1/385; A61B 5/6803; A61B 5/0205; A61B 5/0476; A61B 5/02438; A61B 2562/0219; A61B 5/024; A61B 5/369
See application file for complete search history.

(56) References Cited

U.S. PATENT DOCUMENTS

| | | | |
|---|---|---|---|
| 2015/0074876 A1* | 3/2015 | Chiang | A42B 3/145 2/418 |
| 2016/0167672 A1* | 6/2016 | Krueger | A61B 5/7282 340/576 |
| 2017/0309153 A1* | 10/2017 | Van Oorschot | A61B 5/1116 |

FOREIGN PATENT DOCUMENTS

| | | | | |
|---|---|---|---|---|
| CN | 206262047 U | 6/2017 | | |
| CN | 206365527 U | 8/2017 | | |
| CN | 107594732 A | 1/2018 | | |
| WO | 8902679 A1 | 3/1989 | | |
| WO | WO-2016182974 A1 * | 11/2016 | | A61B 5/04 |
| WO | 2016205757 A1 | 12/2016 | | |

* cited by examiner

HEADBAND AND MULTIFUNCTIONAL HELMET

CROSS REFERENCE TO RELATED APPLICATIONS

This application is a continuation-in-part of International Patent Application PCT/CN2018/101884, filed on Aug. 23, 2018, which claims the benefit of priority of Chinese Application No. CN201711021804X, filed on Oct. 27, 2017, each of which are incorporated herein by reference.

FIELD OF THE INVENTION

The present disclosure relates to the field of riding equipment, and particularly to a headband and a multifunctional helmet.

BACKGROUND OF THE INVENTION

A riding helmet essentially consists of two parts, i.e., a helmet body and a headband. For the existing riding helmets, in order to realize intelligentization, e.g., making and receiving calls and listening to music, the current practice is to embed the electronic accessories inside the helmet body. For example, for an intelligent helmet product of the brand LIVALL, the batteries, cables and earphones thereof are all embedded inside the helmet body. To expand the functions of the helmet body in the above-mentioned fields, it is necessary to embed various relevant assemblies in the helmet body, but this yet poses a lot of problems.

SUMMARY OF THE INVENTION

Some embodiments of the present disclosure can provide a headband. The headband is an accessory of a helmet, electronic devices are combined with the headband such that the headband has electronic functions associated therewith, expanding at least one requirement of the use range of the headband.

The present disclosure provides a multifunctional helmet, in which electronic devices are connected to the headband, the headband is connected to a helmet body, and there is no need to make great modifications to the helmet body, reducing the design difficulty of the helmet.

Embodiments of the present disclosure are implemented as follows:

A headband, comprising a strap configured to bind a head, an adjustment assembly that adjusts the tightness of the strap, and an electronic device that endows the headband with intelligent properties. The strap is connected to the adjustment assembly, and the electronic device is disposed within the adjustment assembly and connected to the adjustment assembly.

The present disclosure provides a multifunctional helmet, comprising a helmet body and the above-described headband, the helmet body being connected to the headband.

BRIEF DESCRIPTION OF DRAWINGS

In order to more clearly illustrate the technical solutions of the embodiments of the present disclosure, brief description is made below on the drawings required to be used in the embodiments. It should be understood that the following drawings only illustrate some of the embodiments of the present disclosure and shall not be regarded as a limitation to the scope, and for a person of ordinary skills in the art, other related drawings may be obtained from these drawings without inventive effort.

Figure 1:
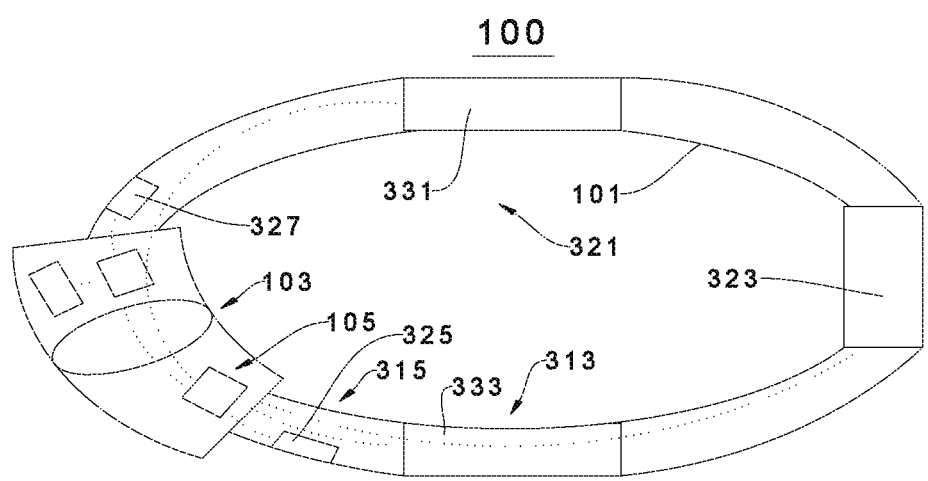
FIG. 1 is a schematic structural diagram of a headband according to an embodiment of the present disclosure.

Reference signs: 100—headband; 210—gear; 220—rack assembly; 221—first rack; 223—second rack; 101—strap; 103—adjustment assembly; 105—electronic device; 201—electronic receptacle; 203—mechanical assembly; 205—mechanical receptacle; 207—first electric wire; 209—second electric wire; 301—power supply; 303—wireless transmission unit; 305—central processor; 307—acceleration sensor; 309—warning light; 311—light intensity sensor; 313—earphone assembly; 321—earphone unit; 323—microphone; 331—first earphone; 333—second earphone; 315—sensor assembly; 325—heart rate sensor; 327—brain wave collector; 400—helmet body; 500—earphone adjustment means; 501—adjustment assembly; and 502—base.

DETAILED DESCRIPTION OF THE INVENTION

In order to make the objects, technical solutions and advantages of the embodiments of the present disclosure clearer, the technical solutions of the embodiments of the present disclosure will be described clearly and completely below with reference to the drawings of the embodiments of the present disclosure. Apparently, the embodiments described are some of the embodiments of the present disclosure, rather than all of the embodiments. The components of the embodiments of the present disclosure described and illustrated in the drawings herein can generally be arranged and designed in a variety of different configurations.

Thus, the following detailed description of the embodiments of the present disclosure provided in the drawings is not intended to limit the scope of the present disclosure claimed, but is merely representative of the selected embodiments of the present disclosure. All the other embodiments that are obtained by a person of ordinary skills in the art without inventive effort on the basis of the embodiments of the present disclosure shall be covered by the protection scope of the present disclosure.

It should be noted that like reference signs and letters denote like items in the drawings, and therefore, once a certain item is defined in one figure, it does not need to be further defined or explained in the following figures.

In the description of the present disclosure, it should be noted that the terms "first", "second", etc. are only used to discriminate the description, but cannot be construed as an indication or suggestion of relative importance.

In the description of the present disclosure, it should be further noted that unless otherwise explicitly specified and defined, the terms "arrange", "communicate", "link" and "connect" shall be understood in broad sense, which may, for example, refer to fixed connection, detachable connection or integral connection; may refer to mechanical connection or electrical connection; may refer to direct connection or indirect connection by means of an intermediate medium; and may refer to communication between two elements. A person of ordinary skills in the art could understand the specific meaning of the terms in the present disclosure according to specific situations.

Some of the embodiments of the present disclosure are described in detail below with reference to the drawings. The following embodiments and the features in the embodiments can be combined with each other if there is no conflict.

A helmet itself is safety equipment, and is not allowed for sale unless various safety tests have been conducted thereon. The embedding of relevant functional assembles therein will affect the safety of the helmet, so special design is required, which increases the design difficulty. When relevant functional assembles are embedded, the production process of the traditional helmets is changed, and the production links are increased, which increases the production difficulty of the helmet body. Moreover, due to the increase in production links, the scrap rate will be increased, which pulls up the cost of the finished helmets; and since there is an electronic device embedded inside the helmet, the damage of the electronics, or the damage of the helmet will cause the product to be scrapped, making it difficult to have after-sales maintenance.

Referring to FIG. 1, the present embodiment provides a headband 100 comprising a strap 101 configured to bind a head, an adjustment assembly 103 that adjusts the tightness of the strap 101, and an electronic device 105 that endows the headband 100 with intelligent properties. The strap 101 is connected to the adjustment assembly 103, and the electronic device 105 is disposed within the adjustment assembly 103 and connected to the adjustment assembly 103.

The strap 101 is mainly capable of grasping the head of a human body, and is connected to the helmet body, so that the helmet can protect the human body. The strap 101 may be a fixing device made of plastic, etc. and with a certain hardness. The headband 100 is merely an auxiliary device of a helmet, the strap 101 has a hollow structure, and through the strap 101 in a hollow structure are embedded a first electric wire 207 and a second electric wire 209 that are electrically connected.

The adjustment assembly 103 not only can adjust the tightness of the strap 101, but also can dispose the electronic device 105 such that the headband 100 has relevant intelligent properties, thereby expanding the use range of the headband 100, and making it unnecessary to design the electronic device 105 on the helmet, which thereby reduces the design difficulty of the helmet and also facilitates the replacement of the electronic device 105.

Figure 2:
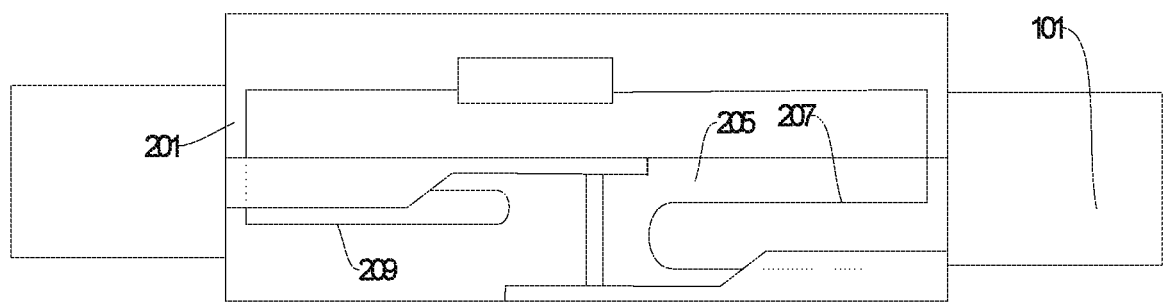
FIG. 2 is a first schematic structural diagram of an adjustment assembly according to an embodiment of the present disclosure.
Figure 3:
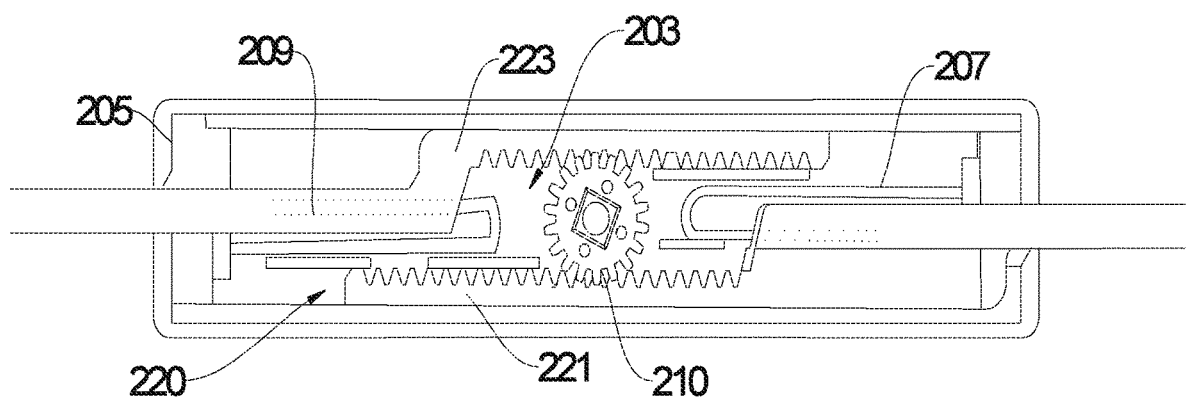
FIG. 3 is a second schematic structural diagram of the adjustment assembly according to an embodiment of the present disclosure.

Referring to FIGS. 2 and 3 in combination, the adjustment assembly 103 comprises an electronic receptacle 201 for receiving the electronic device 105, a mechanical assembly 203 for adjusting the tightness of the strap 101, and a mechanical receptacle 205 for placing an adjustment member. The electronic device 105 is disposed within and connected to the electronic receptacle 201, and the mechanical assembly 203 is disposed within and movably connected to the mechanical receptacle 205. The electronic receptacle 201 and the mechanical receptacle 205 are disposed adjacent to each other to ensure that the mechanical elements and the electronic elements do not interfere with each other, thereby ensuring that each of the mechanical elements and the electronic elements can operate normally, and extending the service life of each of the mechanical elements and the electronic elements as much as possible.

The mechanical assembly 203 comprises a gear 210 and a rack assembly 220. The gear 210 is placed within and movably connected to the mechanical receptacle 205, the rack assembly 220 is meshingly connected to the gear 210, and the rack assembly 220 is slidably connected to the mechanical receptacle 205. The gear 210 drives the rack assembly 220 to slide within the mechanical receptacle 205, thereby tightening or relaxing the headband 100. By means of the connection between the gear 210 and the rack assembly 220, a simple structure can be achieved, which simplifies the structure of the headband 100.

Further, the rack assembly 220 comprises a first rack 221 and a second rack 223. The first rack 221 and the second rack 223 are located on the two sides of the gear 210, respectively, and are both meshingly connected to the gear 210. The first rack 221 and the second rack 223 are both movably connected to the mechanical receptacle 205. The rack assembly 220 is provided with two racks so that a user can adjust the size of the headband 100 in different directions. When the first rack 221 and the second rack 223 simultaneously move towards each other in a direction close to the gear 210, the distance between the first rack 221 and the second rack 223 becomes shorter, so that the headband 100 becomes smaller and grasps the user's head, thereby increasing the action force of the headband 100 upon the user's head, and ensuring the safety of the helmet and preventing the helmet from falling off. When the first rack 221 and the second rack 223 simultaneously move away from each other in a direction away from the gear 210, the distance between the first rack 221 and the second rack 223 becomes relatively longer, so that the size of the headband 100 is increased, the action force between the headband 100 and the user's head becomes smaller, which facilitates the user's taking off the helmet.

Further, the headband 100 further comprises a plurality of first electric wires 207 and a plurality of second electric wires 209 for transmitting various signals, the plurality of first electric wires 207 are connected to the first rack 221, the mechanical receptacle 205, the electronic receptacle 201 and the electronic device 105, and the plurality of second electric wires 209 are connected to the second rack 223, the mechanical receptacle 205, the electronic receptacle 201 and the electronic device 105. Specifically, the plurality of first electric wires 207 and the plurality of second electric wires 209 are both partially located within the mechanical receptacle 205, and are both partially located within the electronic receptacle 201, that is, the moving of the mechanical assembly 203 in the mechanical receptacle 205 will drive the first electric wires 207 and the second electric wires 209 to move in the first rack 221, the second rack 223 and the mechanical receptacle 205, making it possible to ensure the normal operation of the electronic elements in the electronic receptacle 201 and ensure that the mechanical assembly 203 can effectively adjust the tightness of the headband 100.

Specifically, when the first rack 221 and the second rack 223 move towards each other, that is, the overlapping portion between the first rack 221 and the second rack 223 becomes increasingly large, a portion of the first electric wire 207 within the first rack 221 is pushed out of the first rack 221 and is then folded within the mechanical receptacle 205, which thereby adjusts the relative length of the first electric wire 207. When the first rack 221 and the second rack 223 move in opposite directions, i.e., the overlapping portion between the first rack 221 and the second rack 223 gradually decreases, the folded portion in the mechanical receptacle 205 moves away from the gear 210 with the movement of the rack, and when the overlapping portion between the first gear 210 and the second gear 210 is minimized, the first electric wire 207 appears as a straight line. The second electric wire 209 moves in the same manner as the first electric wire 207, but only in the opposite direction.

Figure 4:
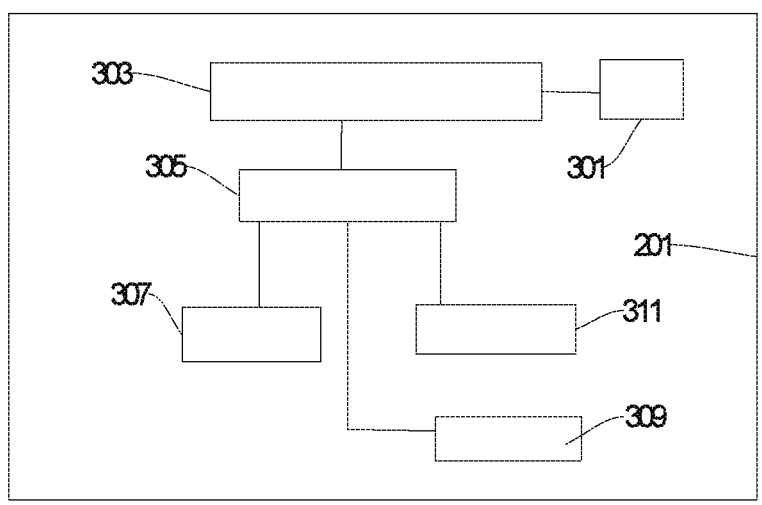
FIG. 4 is a schematic structural diagram of an electronic device according to an embodiment of the present disclosure.
Figure 5:
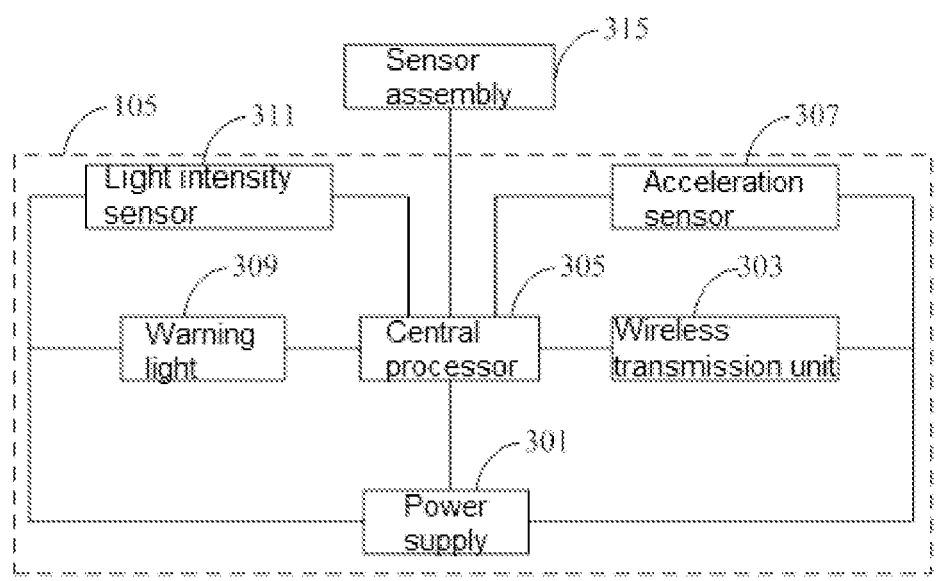
FIG. 5 is a block diagram of a circuit structure of an electronic device according to an embodiment of the present disclosure.

Referring to FIGS. 4 and 5, the electronic device 105 comprises a power supply 301, a wireless transmission unit 303, a central processor 305, an acceleration sensor 307, a warning light 309 and a light intensity sensor 311. The power supply 301 is electrically connected to all of the wireless transmission unit 303, the central processor 305, the acceleration sensor 307, the warning light 309 and the light intensity sensor 311, and the central processor 305 is electrically connected to all of the acceleration sensor 307, the warning light 309 and the light intensity sensor 311.

Further, the power supply 301 is configured to supply power to the wireless transmission unit 303, the central processor 305, the acceleration sensor 307, the warning light 309 and the light intensity sensor 311. The power supply 301 is disposed within and connected to the electronic receptacle 201. The connection between the power supply 301 and the electronic receptacle 201 may be a fixed connection, e.g., fixed by a bolt, and fixed by glue, and also may be a detachable connection to facilitate replacement for a new battery, e.g., snap-fit connection, and connection by Velcro tape. The power supply 301 may be a dry cell, a storage battery, a supercapacitor or the like.

Further, the electronic device 105 also comprises the wireless transmission unit 303, which may be communicatively connected to a user's mobile terminal (e.g., a smart phone, a wearable mobile terminal, a tablet computer, etc.), and is configured to enable data interaction between the electronic device 105 and the user's mobile terminal. The wireless transmission unit 303 is disposed in and connected to the electronic receptacle 201, and the wireless transmission unit 303 may be Bluetooth, WLAN (Wireless Local Area Networks), NFC (Near Field Communication), RFID (Radio Frequency Identification) and other short-distance communication chips, and may also be 2G/3G/4G and other long-distance communication chips.

Further, the electronic device 105 also comprises the central processor 305. The central processor 305 has signal processing capability, and can also control the wireless transmission unit 303, the acceleration sensor 307, the warning light 309 and the light intensity sensor 311. The central processor 305 is disposed in and connected to the electronic receptacle 201, and is electrically connected to the wireless transmission unit 303. The wireless transmission unit 303 transmits a received signal to the central processor 305, and the central processor 305 processes the signal and sends out a related processing operation signal. As an embodiment, a digital signal processor, an application specific integrated circuit, a field programmable gate array or other programmable logic devices, a discrete gate or transistor logic device, a discrete hardware component, etc. may also be employed to replace the central processor 305, so as to control the wireless transmission unit 303, the acceleration sensor 307, the warning lamp 309, and the light intensity sensor 311.

Further, the electronic device 105 also comprises the acceleration sensor 307. The acceleration sensor 307 is disposed within and connected to the electronic receptacle 201. The acceleration sensor 307 is configured to collect acceleration data of the user in real time during riding, and transmit the collected acceleration data to the central processor 305, so that the central processor 305 analyzes and processes the acceleration data, so as to determine the intensity of the user's motion, whether there is a tumble or not, etc. When it is determined that the user's motion is severe or there is a tumble, the central processor 305 will control the warning light 309 to be turned on, which serves the function of warning, and thereby ensures the safety of the rider. In addition, the central processor 305 may also transmit the acceleration data to the mobile terminal of the user through the wireless transmission unit 303, so that the user may know his motion state through the mobile terminal.

It should be noted that a gyroscope may further be provided for the acceleration sensor 307 to enhance the acceleration sensor, so that it is possible to improve the stability of the acceleration data collected by the acceleration sensor 107, and further improve the accuracy of the central processor 305 in determining the intensity of the user's motion, whether there is a tumble or not, etc.

Further, the electronic device 105 also comprises the warning light 309. The warning light 309 is disposed outside and connected to the electronic receptacle 201. The warning light 309 is electrically connected to the central processor 305. The warning light 309 is disposed on an upper surface of the electronic receptacle 201. The warning light 309 is configured to be turned on under the control of the central processor 305, so as to serve the function of warning or ensuring the safety of riding in the dark night. Optionally, the warning light 309 is an LED light.

Preferably, the electronic device 105 further comprises the light intensity sensor 311. The light intensity sensor 311 is disposed within and connected to the electronic receptacle 201. The light intensity sensor 311 is electrically connected to the central processor 305. The light intensity sensor 311 is configured to receive an optical signal from an external environment, and convert the optical signal into an electric signal, and then transmit the electric signal to the central processor 305, so that the central processor 305 determines the intensity of the light according to the electric signal. When determining that the external environment light is weak, the central processor 305 controls the warning light 309 to be turned on, which serves the function of automatically controlling the light. By providing the light intensity sensor 311, it is possible to improve the degree of intelligentization of the headband 100, so that the warning light 309 can be automatically turned on or off according to the degree of illumination of the external environment, so as to facilitate riding in a dark environment, such as in a tunnel.

Further, the headband 100 also comprises an earphone assembly 313. The earphone assembly 313 is connected to the strap 101. The earphone assembly 313 is communicatively connected to the electronic device 105. Specifically, the earphone assembly 313 is communicatively connected to the wireless transmission unit 303 through the first electric wire 207 and the second electric wire 209. The wireless transmission unit 303 may transmit an audio signal of a mobile device (e.g. smart phone) to the electronic device 105, and the electronic device 105 transmits the audio signal to the earphone, so that the user can listen to music through the earphone in the riding process, thereby meeting the user's requirement of listening to music during the riding.

Further, the earphone assembly 313 comprises an earphone unit 321 and a microphone 323. The earphone unit 321 and the microphone 323 are both connected to the strap 101, and the earphone unit 321 and the microphone 323 are both connected to the electronic device 105. The earphone is configured to receive an audio signal transmitted by the electronic device 105, and the microphone 323 is configured to pick up a human voice.

Further, the earphone unit 321 comprises a first earphone 331 and a second earphone 333. The first earphone 331 and the second earphone 333 are both connected to the strap 101, and the first earphone 331 and the second earphone 333 are disposed opposite to each other. The first earphone 331 and the second earphone 333 are both communicatively connected to the wireless transmission unit 303.

Further, the headband 100 also comprises a sensor assembly 315. The sensor assembly 315 is disposed within and connected to the strap 101. The sensor assembly 315 is electrically connected to the electronic device 105. That is, the sensor assembly 315 is electrically connected to the central processor 305 and is electrically connected to the power supply 301. The power supply 301 may supply power to the sensor assembly 315, and the central processor 305 may analyze and process the signals collected by the sensor assembly 315.

Further, the sensor assembly 315 comprises a heart rate sensor 325 and a brain wave collector 327. The heart rate sensor 325 and the brain wave collector 327 are both disposed within and connected to the strap 101, and the heart rate sensor 325 and the brain wave collector 327 are both electrically connected to the central processor 305 and to the power supply 301.

The heart rate sensor 325 is configured to collect heart rate data of the user during riding and transmit the heart rate data to the central processor 305, so that the central processor 305 analyzes and processes the heart rate data, so as to monitor whether the heart rate of the user is abnormal in the riding process. When monitoring abnormal heart rate of the user, the central processor 305 will control the warning light 309 to be turned on, which serves the function of warning to ensure the safety of the rider. In addition, the brain wave collector 327 is configure to collect brain wave data of the user during the riding and transmit the brain wave data to the central processor 305, so that the central processor 305 analyzes and processes the brain wave data to obtain the mental state of the user. When monitoring poor mental state of the user, the central processor 305 will control the warning light 309 to be turned on, which serves the function of warning, so as to prevent the user from over exercise. In addition, the central processor 305 may also transmit the heart rate data and the brain wave data to the mobile terminal of the user through the wireless transmission unit 303, so that the user may know, through the mobile terminal, his health status when in motion (exercise).

The present disclosure further provides a multifunctional helmet, comprising a helmet body 400 and the above-described headband 100, the helmet body 400 being connected to the headband 100.

Further, the headband 100 of the multifunctional helmet provided in the present disclosure has the above-described structure, which therefore will not be further described here.

Figure 6:
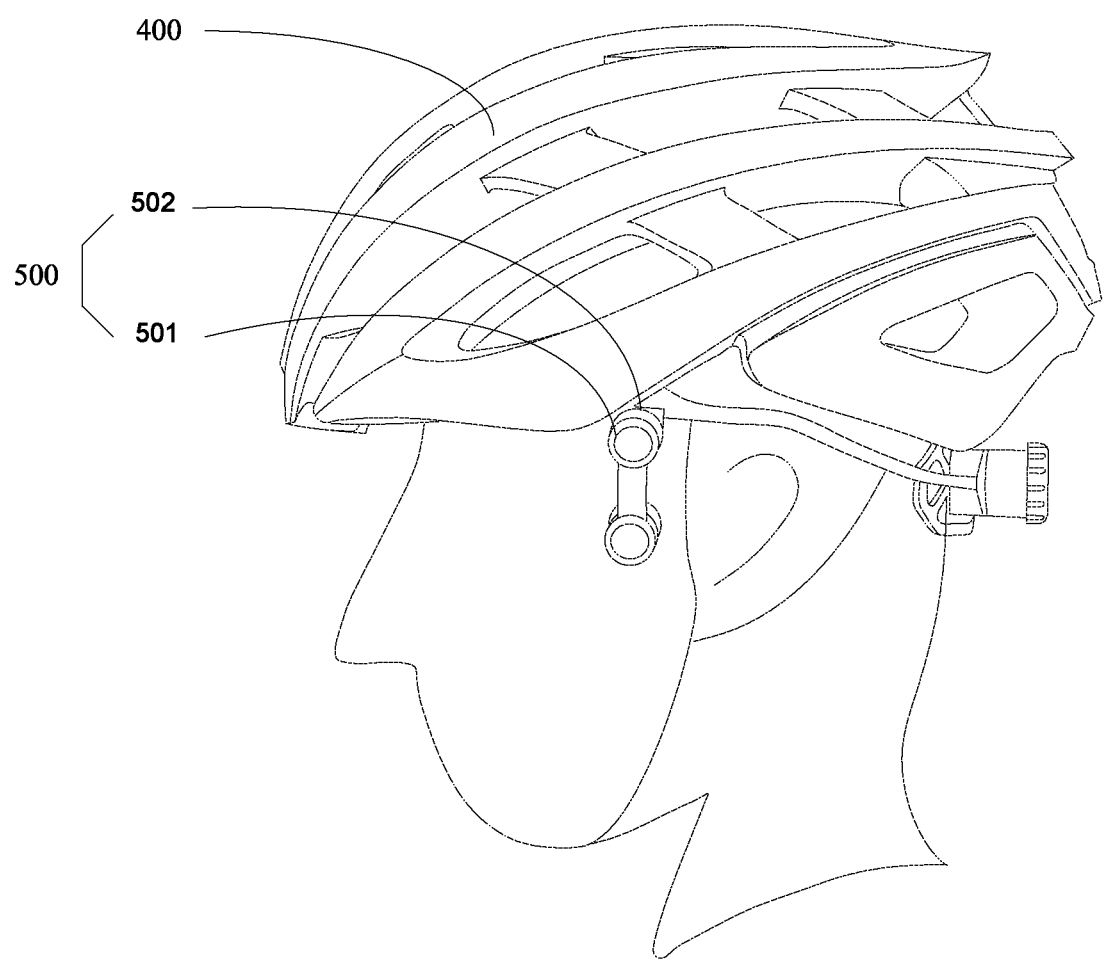
FIG. 6 is a schematic structural diagram of a multifunctional helmet according to an embodiment of the present disclosure.

Referring to FIG. 6, further, the present disclosure also provides a multifunctional helmet, further comprising earphone adjustment means 500. The earphone adjustment means 500 comprises an adjustment assembly 501 capable of adjusting the rotational angle and the horizontal height of a sound generating unit, and a base 502 for mounting the adjustment assembly. The adjustment assembly 501 is fixedly connected to the base 502.

The adjustment assembly 501 implements the main adjustment functions of the earphone adjustment means 500. Optionally, the adjustment assembly 501 comprises a rotation assembly capable of adjusting the rotational angle of the sound generating unit, one end of the rotation assembly being fixedly connected to the base; the rotation assembly not only can rotate the sound generating unit to an appropriate angle, but also can adjust the height of the sound generating unit during the rotation, to accommodate (receive) the earphone, thereby improving the portability of the earphone.

Optionally, the rotation assembly comprises a fixed shaft and a lifting member. The fixed shaft is fixedly connected to the base, and one end of the lifting member is sleeved on the fixed shaft and is rotationally connected to the fixed shaft. The fixed shaft is fixedly connected to the base, the fixed shaft does not rotate, and the lifting member rotates about the fixed shaft. Meanwhile, the lifting member can rotate from one end of the fixed shaft close to the base, along the outer circumference of the fixed shaft to the other end of the fixed shaft relatively away from the base, thereby achieving the adjustment in height and the adjustment in angle.

In summary, for the headband and the multifunctional helmet provided in the present disclosure, the multifunctional helmet comprises a helmet body and the headband, the helmet body is connected to the headband, and the headband comprises a strap configured to bind a head, an adjustment assembly that adjusts the tightness of the strap, and an electronic device that endows the headband with intelligent properties. The strap is connected to the adjustment assembly, and the electronic device is disposed within the adjustment assembly and connected to the adjustment assembly. In the present disclosure, by providing the electronic device, the electronic device and the headband are integrally formed, which reduces the space occupied by the electronic device, and also facilitates the replacement of the electronic device. Moreover, by integrally forming the electronic device and the headband, there is no need to embed wires in the helmet body, then it is unnecessary to make great modifications to the helmet, thereby reducing the design difficulty of the helmet and reducing the production difficulty of the helmet.

The description above is merely preferred embodiments of the present disclosure, which are not used to limit the present disclosure. For a person skilled in the art, the present disclosure may have various changes and variations. Any modifications, equivalent substitutions, improvements etc. within the spirit and principle of the present disclosure shall all be included in the scope of protection of the present disclosure.

INDUSTRIAL APPLICABILITY

The present disclosure provides a headband and a multifunctional helmet, wherein an electronic device is incorporated into the headband, so that the electronic device and the headband are integrally formed, which reduces the space occupied by the electronic device, and also facilitates the replacement of the electronic device.

The invention claimed is:
1. A helmet comprising:
a helmet body; and
a headband connected to the helmet body, wherein the headband includes:
 a strap adapted to bind to a head of a user; and an adjustment assembly adapted to adjust a tightness of the strap, the adjustment assembly comprising:
- a mechanical receptacle comprising a mechanical assembly adapted to adjust a tightness of the strap, the mechanical assembly comprising a gear, a first rack connected to the gear and a second rack connected to the gear, wherein the gear is adapted to cause a movement of the first and second racks;
- an electronic receptacle comprising an electronic device;
- a plurality of first wires connected to the electronic device, the mechanical receptacle, the electronic receptacle, and the first rack; and
- a plurality of second wires connected to the electronic device, the mechanical receptacle, the electronic receptacle, and the second rack;
- wherein movement of the first and second racks towards each other increases a portion of a first length of the first wire as the first wire is pushed out of the first rack and increases a portion of a second length of the second wire as the second wire is pushed out of the first rack; and
- wherein movement of the first and second racks is in opposite directions from each other, the portion of the first length of the first wire decreases as the first wire is folded within the mechanical receptacle and the portion of the second length of the second wire decreases as the second wire is folded within the mechanical receptacle.

2. The helmet according to claim 1, wherein the first and second racks are slidably connected to the mechanical receptacle.

3. The helmet according to claim 2, wherein the first rack and the second rack are located on first and second sides of the gear respectively, and the first rack and the second rack are meshingly connected to the gear.

4. The helmet according to claim 1, wherein the electronic device comprises a wireless transmission unit which is disposed in and connected to the electronic receptacle.

5. The helmet according to claim 4, wherein the electronic device comprises a central processor which is disposed in and connected to the electronic receptacle, and electrically connected to the wireless transmission unit.

6. The helmet according to claim 5, wherein the electronic device further comprises a warning light which is disposed outside and connected to the electronic receptacle, and electrically connected to the central processor.

7. The helmet according to claim 6, wherein the electronic device further comprises an acceleration sensor which is disposed within and connected to the electronic receptacle, and electrically connected to the central processor.

8. The helmet according to claim 5, wherein the electronic device further comprises a light intensity sensor which is disposed within and connected to the electronic receptacle, and electrically connected to the central processor.

9. The helmet according to claim 5, comprising a sensor assembly which is disposed within and connected to the strap, and electrically connected to the electronic device.

10. The helmet according to claim 9, wherein the sensor assembly comprises a heart rate sensor and a brain wave collector, which are disposed within and connected to the strap, and electrically connected to the central processor.

11. The helmet according to claim 1, further comprising an earphone assembly which is connected to the strap and communicatively connected to the electronic device.

12. The helmet according to claim 11, wherein the earphone assembly comprises an earphone unit and a microphone, which are connected to the strap and connected to the electronic device.

13. The helmet according to claim 1, wherein the adjustment assembly comprises an electronic receptacle for receiving the electronic device, a mechanical assembly for adjusting the tightness of the strap, and a mechanical receptacle for an adjustment member to be placed, the electronic device is disposed within and connected to the electronic receptacle, and the mechanical assembly is disposed within and movably connected to the mechanical receptacle.

14. The helmet according to claim 1, wherein the electronic device comprises a wireless transmission unit, a central processor, a warning light, an acceleration sensor and a light intensity sensor;
- the wireless transmission unit is disposed in and connected to the electronic receptacle; the central processor is disposed in and connected to the electronic receptacle, and electrically connected to the wireless transmission unit; the warning light is disposed outside and connected to the electronic receptacle, and electrically connected to the central processor; the acceleration sensor is disposed within and connected to the electronic receptacle, and electrically connected to the central processor; and the light intensity sensor is disposed within and connected to the electronic receptacle, and electrically connected to the central processor.

15. The helmet according to claim 1, wherein the headband further comprises a sensor assembly which is disposed within and connected to the strap, and electrically connected to the electronic device.

16. The helmet according to claim 1, wherein the headband further comprises an earphone assembly which is connected to the strap and communicatively connected to the electronic device.

* * * * *